United States Patent [19]

Kitano et al.

[11] Patent Number: 5,066,813

[45] Date of Patent: Nov. 19, 1991

[54] METHOD FOR PRODUCTION OF 1,3-THIAZOLIDIN-2-ONES

[75] Inventors: Masao Kitano, Kamakura; Mitsuaki Yagisawa, Kawasaki; Yutaka Morimoto, Yokohama, all of Japan

[73] Assignee: Nippon Shokubai Kagaku Kogyo Co., Ltd., Osaka, Japan

[21] Appl. No.: 489,672

[22] Filed: Mar. 7, 1990

[30] Foreign Application Priority Data

Mar. 8, 1989 [JP] Japan .................................. 1-53867

[51] Int. Cl.$^5$ ............................................ C07D 277/14
[52] U.S. Cl. .................................................... 548/182
[58] Field of Search ........................................ 548/182

[56] References Cited

FOREIGN PATENT DOCUMENTS 50-117772  9/1975  Japan .
127466  11/1978  Japan .................................. 548/182
61-30580  2/1986  Japan .
62-84067  4/1987  Japan .

OTHER PUBLICATIONS

Potts, Comprehensive Heterocyclic Chemistry, 6, p. 273 (1984).
Michels, J. A. C. S., 78, p. 5349 (1956).

*Primary Examiner*—Robert Gerstl
*Attorney, Agent, or Firm*—Burns, Doane, Swecker & Mathis

[57] ABSTRACT

A method for the production of a 1,3-thiazolidin-2-one represented by the general formula II:

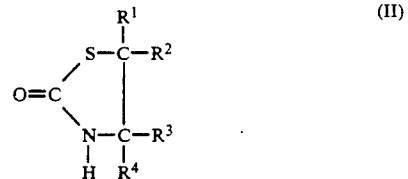

(II)

wherein $R^1$, $R^2$, $R^3$, and $R^4$ are independently hydrogen atom or a lower alkyl group, which method comprises causing a 1,3-thiazolidine represented by the general formula I:

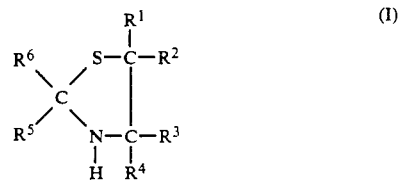

(I)

wherein $R^1$, $R^2$, $R^3$, $R^4$, $R^5$, and $R^6$ are independently hydrogen atom or a lower alkyl group to react with urea.

3 Claims, No Drawings

METHOD FOR PRODUCTION OF 1,3-THIAZOLIDIN-2-ONES

BACKGROUND OF THE INVENTION

1. Field of the Invention

This invention relates to a method for the production of 1,3-thiazolidin-2-ones. More particularly, it relates to a method for the production of 1,3-thiazolidin-2-one from 1,3-thiazolidines.

2. Description of the Prior Art 1,3-Thiazolidin-2-one are useful as intermediates for medicines and agricultural pesticides. To date, the following methods have been proposed for the production of these compounds.

(A) A method disclosed in "Journal of American Chemical Society," vol 78, page 5350 (1956), which effects the production by fusing cysteamine hydrochloride and urea and allowing them to react with each other.

(B) A method disclosed in Japanese Patent Laid-Open SHO 62(1987)-84,067, which attains the production by causing 2-aminoethyl sulfate or 2-chloroethyl amine hydrochloride to react with carbonyl sulfide in the presence of a deacidifying agent.

(C) A method disclosed in Japanese Patent laid-Open SHO 61(1986)-30,580, which obtains the production by causing 1,3-oxazolidin-2-one to react with hydrogen sulfide under application of pressure.

(D) A method disclosed in Japanese Patent Laid-Open SHO 50(1975)-117,772, which accomplishes the production by cysteamine to react with carbon monoxide in the presence of selenium and a tertiary amine.

The conventional methods mentioned above, however, have various drawbacks of their own. The method of (A) has the problem of disposing of an inorganic salt by-produced in a large amount by the reaction and entails the disadvantage that the reaction product necessitates a complicate treatment for purification. The method of (B), similarly to that of (A), entails the problem of disposal of a by-produced inorganic salt and the disadvantage that the raw material, carbonyl sulfide, is not easily obtained commercially. The method of (C) has the disadvantage that hydrogen sulfide, a noxious substance, undergoes the reaction under application of pressure and the reaction requires use of 1,3-oxazolidin-2-one, a compound not readily obtained as a raw material. Then, the method of (D) inevitably necessitates use of expensive selenium as a catalyst. Because of the various drawbacks described above, these conventional methods are not advantageous for commercial production of 1,3-thiazolidin-2-ones.

An object of this invention, therefore, is to provide a novel method for the production of 1,3-thiazolidin-2-ones.

Another object of this invention is to provide an economic method for the production of 1,3-thiazolidin-2-ones.

SUMMARY OF THE INVENTION

The objects described above are accomplished by a method for the production of a 1,3-thiazolidin-2-one represented by the general formula II:

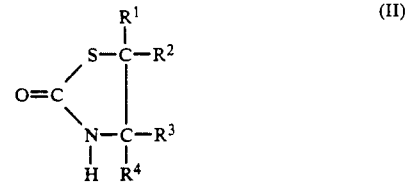

wherein $R^1$, $R^2$, $R^3$ and $R^4$ are independently a hydrogen atom or a lower alkyl group, which method comprises causing a 1,3-thiazolidine represented by the general formula I:

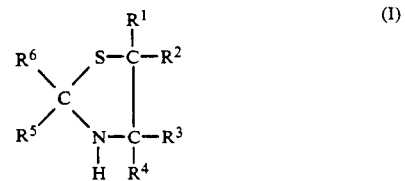

wherein $R^1$, $R^2$, $R^3$, $R^4$, $R^5$, and $R^6$ are independently hydrogen atom or a lower alkyl group, to react with urea.

EXPLANATION OF THE PREFERRED EMBODIMENT

The 1,3-thiazolidines to be used in the method of this invention are compounds represented by the general formula I mentioned above. In the formula, $R^1$, $R^2$, $R^3$, $R^4$, $R^5$ and $R^6$ are independently hydrogen atom or a lower alkyl group. The number of carbon atoms of the alkyl group is preferable to be in the range of 1 to 4. Specifically, the 1,3-thiazolidines which are usable herein include 3-thiazolidine, 2-methyl-1,3-thiazolidine, 2,2-dimethyl-1,3-thiazolidine, 2-methyl-2-ethyl-1,3-thiazolidine, 2-methyl-2-isobutyl-1,3-thiazolidine, 2,2,4-trimethyl-1,3-thiazolidine, 2,2,4,5-tetramethyl-1,3-thiazolidine, 2,2-dimethyl-4-ethyl-1,3-thiazolidine, 2,2-dimethyl-5-ethyl-1,3-thiazolidine, 2,4-dimethyl-2-ethyl-1,3-thiazolidine, 2,5-dimethyl-2-ethyl-1,3-thiazolidine, 2,4-dimethyl-2-isobutyl-1,3-thiazolidine, 2,5-dimethyl-2-isobutyl-1,3-thiazolidine, and 2,4,5-trimethyl-2-isobutyl-1,3-thiazolidine, for example.

The reaction of such a 1,3-thiazolidine as mentioned above with urea is carried out either not in any solvent or in an organic solvent or water. The organic solvent, when used at all in the reaction, is required to be inactive to the reaction.

The 1,3-thiazolidine and urea to be used in the reaction of this invention are generally in such amounts that the molar ratio of urea to 1,3-thiazolidine is 1:1. Though this molar ratio is not critical, the amount of urea is generally preferable to be in the range of 0.5 to 3 mols. Per mol of 1,3-thiazolidine.

The reaction temperature is in the range of 80° to 200° C., preferably 100° to 180° C. Though the reaction time is variable with the kinds of raw materials to be used, it generally falls in the range of 1 to 10 hours.

After the reaction is completed, the produced 1,3-thiazolidin-2-one can be obtained in high purity easily by distilling the reaction solution. Optionally, the product of the reaction, when necessary, may be obtained in the form of crystals of high purity by distilling the reaction solution thereby expelling the used solvent and recrystallizing the residue of distillation from an alcohol such as methanol or ethanol or from a mixed solvent of hexane and ethyl acetate.

By executing this invention, 1,3-thiazolidin-2-ones which are useful as intermediates for medicines and agricultural pesticides can be produced advantageously from the economic point of view.

Now, the present invention will be described more specifically below with reference to working examples. It should be noted, however, that these examples do not restrict the method of this invention in any sense.

EXAMPLE 1

In a four-neck flask having an inner volume of 500 ml and provided with a stirrer, a thermometer, and a condenser, 210.6 g of 2,2-dimethyl-1,3-thiazolidine and 108.0 g of urea were stirred and heated. When the temperature of the reaction mixture rose to the neighborhood of 120° C., it was melted into a uniform solution. It was further heated to 160° C. and left undergoing reaction. In this while, since ammonia was emanated from the top of the condenser, the reaction was continued with the emanating ammonia kept absorbed in an aqueous hydrochloric acid solution. When the reaction was continued for two hours following the rise of the temperature to 160° C., the emanation of ammonia ceased and the reaction was completed. On analysis by gas chromatography, the reaction solution was found to contain 133 g of 1,3-thiazolidin-2-one, representing a yield of 72% based on 2,2-dimethyl-1,3-thiazolidine. When this reaction solution was distilled under a vacuum, there was obtained 1,3-thiazolidin-2-one with a purity of not less than 98% as determined by gas chromatography.

EXAMPLE 2

In the same apparatus as used in Example 1, 210.6 g of 2,2-dimethyl-1,3-thiazolidine and 216 g of urea were left reacting at 160° C. for 3 hours. Similarly to the experiment of Example 1, the ammonia emanating from the reaction mixture was absorbed in an aqueous hydrochloric acid solution. On analysis by gas chromatography, the reaction solution obtained at the end of the reaction was found to contain 137 g of 1,3-thiazolidin-2-one, representing a yield of 74% based on 2,2-dimethyl-1,3-thiazolidine.

By recrystallizing the reaction solution from methanol, there were obtained crystals of 1,3-thiazolidin-2-one having a melting point of 49° to 51° C.

EXAMPLE 3

In a four-neck flask having an inner volume of 500 ml and provided with a stirrer, a thermometer, and a solvent distilling device, 210.6 g of 2,2-dimethyl-1,3-thiazolidine, 108 g of urea, and 97 g of water were stirred at 100° to 120° C. for 6 hours. The resultant reaction mixture was heated to 160° C. and then left undergoing reaction at that temperature for two hours, with water expelled from the reaction system by distillation.

On analysis by gas chromatography, the reaction solution obtained at the end of the reaction was found to contain 143 g of 1,3-thiazolidin-2-one, representing a yield of 77% based on 2,2-dimethylthiazolidine.

EXAMPLE 4

In the same apparatus as used in Example 1, 173 g of 2,4-dimethyl-2-isobutyl-1,3-thiazolidine and 60 g of urea were left reacting at 160° C. for 3 hours. Similarly to the experiment of Example 1, the ammonia emanating from the reaction mixture was absorbed in an aqueous hydrochloric acid solution. On analysis by has chromatography, the reaction solution obtained at the end of the reaction was found to contain 78 g of 4-methyl 1,3-thiazolidin-2-one, representing a yield of 67% based on 2,4-dimethyl-2-isobutyl-1,3-thiazolidine.

What is claimed is:

1. A method for the production of 1,3-thiazolidin-2-one which comprising causing 2,2-dimethyl-1,3-thiazolidine with urea in the absence of water at a temperature of 80° to 200° C.

2. A method according to claim 1, wherein said reaction is carried out in the absence of a solvent.

3. A method according to claim 1, wherein said reaction is carried out in the presence of an organic solvent.

* * * * *